United States Patent
Ogawa et al.

(10) Patent No.: US 10,870,223 B2
(45) Date of Patent: Dec. 22, 2020

(54) METHOD OF MANUFACTURING NEEDLE-LIKE ARRAY SHEET

(71) Applicant: FUJIFILM Corporation, Tokyo (JP)

(72) Inventors: Shotaro Ogawa, Kanagawa (JP); Keio Okano, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 209 days.

(21) Appl. No.: 15/695,014

(22) Filed: Sep. 5, 2017

(65) Prior Publication Data
US 2018/0065280 A1    Mar. 8, 2018

(30) Foreign Application Priority Data

Sep. 6, 2016 (JP) ................... 2016-173483

(51) Int. Cl.
  *B29C 39/02*       (2006.01)
  *B29C 41/22*       (2006.01)
  (Continued)

(52) U.S. Cl.
  CPC ....... *B29C 39/025* (2013.01); *A61M 37/0015* (2013.01); *B29C 37/0053* (2013.01);
  (Continued)

(58) Field of Classification Search
  CPC .................................. B29C 39/00; B81C 1/00
  See application file for complete search history.

(56) References Cited

U.S. PATENT DOCUMENTS

| 10,045,936 B2 | 8/2018 | Mochizuki et al. |
| 2011/0192562 A1* | 8/2011 | Motoi ............ A61M 37/0015 163/5 |

(Continued)

FOREIGN PATENT DOCUMENTS

| JP | 2012196426 | 10/2012 |
| JP | 2013153866 | 8/2013 |
| JP | 2015116335 | 6/2015 |
| JP | 2015136422 | 7/2015 |
| JP | 2016106757 | 6/2016 |
| WO | 2014077242 | 5/2014 |

OTHER PUBLICATIONS

"Search Report of European Counterpart Application" dated Feb. 14, 2018, p. 1-p. 6.

(Continued)

*Primary Examiner* — Jacob T Minskey
*Assistant Examiner* — Virak Nguon
(74) *Attorney, Agent, or Firm* — JCIPRNET (57) ABSTRACT

A method of manufacturing a needle-like array sheet includes supplying a first needle-like array-forming solution consisting of an aqueous solution on a first mold having a first recess; interrupting drying in a wet state and forming a needle-like distal end part; supplying a second needle-like array-forming solution consisting of an aqueous solution on a second mold having a second recess; peeling a sheet part molding product, which is dried and solidified and has a protrusion corresponding to the second recess, after the sheet part molding product is formed; inserting the protrusion of the sheet part molding product into the first recess of the first mold; drying and solidifying the needle-like distal end part and the sheet part molding product after inserting the protrusion, bonding the needle-like distal end part and the protrusion of the sheet part molding product together, and forming a needle-like array sheet having the needle-like array.

7 Claims, 6 Drawing Sheets

(51) Int. Cl.
*B29C 37/00* (2006.01)
*A61M 37/00* (2006.01)
*B29C 35/02* (2006.01)
*B29K 105/00* (2006.01)
*B29L 31/00* (2006.01)

(52) U.S. Cl.
CPC ..... *B29C 41/22* (2013.01); *A61M 2037/0053* (2013.01); *A61M 2037/0061* (2013.01); *B29C 35/02* (2013.01); *B29K 2105/0073* (2013.01); *B29K 2995/006* (2013.01); *B29L 2031/756* (2013.01); *B29L 2031/7544* (2013.01)

(56) References Cited

U.S. PATENT DOCUMENTS

| | | |
|---|---|---|
| 2012/0078189 A1 | 3/2012 | Ogawa et al. |
| 2014/0005606 A1* | 1/2014 | Chen ............. A61K 9/0021 604/173 |
| 2014/0272101 A1* | 9/2014 | Chen ............. A61K 9/0021 427/2.21 |
| 2015/0196746 A1 | 7/2015 | Ogawa et al. |
| 2015/0238413 A1 | 8/2015 | Mochizuki et al. |
| 2015/0238434 A1 | 8/2015 | Yoshida et al. |
| 2015/0238743 A1 | 8/2015 | Che et al. |
| 2016/0045720 A1* | 2/2016 | Suzuki ............ A61M 37/0015 604/46 |
| 2016/0082626 A1* | 3/2016 | Kato ............. A61M 37/0015 264/232 |
| 2016/0158511 A1* | 6/2016 | Jin ............. A61K 9/0021 604/173 |
| 2017/0189660 A1* | 7/2017 | Baek ............. B29C 39/42 |
| 2017/0348880 A1* | 12/2017 | Yamada ............. A61M 37/00 |
| 2019/0134368 A1* | 5/2019 | Nagai ............. A61M 37/00 |

OTHER PUBLICATIONS

Office Action of Japan Counterpart Application, with English translation thereof, dated Jul. 2, 2019, pp. 1-7.

* cited by examiner

METHOD OF MANUFACTURING NEEDLE-LIKE ARRAY SHEET

CROSS-REFERENCE TO RELATED APPLICATIONS

The present application claims priority under 35 U.S.C. § 119 to Japanese Patent Application No. 2016-173483, filed on Sep. 6, 2016. The above application is hereby expressly incorporated by reference, in its entirety, into the present application.

BACKGROUND OF THE INVENTION

1. Field of the Invention

The present invention relates to a method of manufacturing a needle-like array sheet, and particularly, to a method of manufacturing a needle-like array sheet based on two-layer molding for concentrating a desired material on a needle distal end.

2. Description of the Related Art

In recent years, functional sheets in which high aspect ratio structures, such as microneedles, are formed on a surface have attracted attention. Also in the field of medical technology, needle-like array sheets in which microneedles that are needle-like protrusions are formed on a surface have been suggested as percutaneous absorption sheets for efficiently administering a medicine to the body via the skin. Since the percutaneous absorption sheets require the medicine to be administered to the human body without giving a pain, it is preferable that the microneedles are thin, the aspect ratio is high, and the distal ends have a shape as sharp as possible.

The needle-like array sheets can be manufactured by cast molding, injection molding, or the like using a concave array mold in which needle-like recesses, which are reversal shapes of the microneedles, are formed. Additionally, in the manufacture of the percutaneous absorption sheets, the percutaneous absorption sheets having a medicine only at the distal ends of the microneedles are manufactured by filling distal ends of the needle-like recesses of the concave array mold with a liquid containing the expensive medicine and thereafter, supplying a liquid not containing the medicine thereto. By having the medicine only at the distal ends, the medicine can be effectively administered to a human body.

As a method of manufacturing sheets having needle-like bodies, such as the needle-like array sheets, for example, a method of manufacturing a needle-like body by making a needle-like precursor in which puncturing needle parts are provided from a second engraved plate using resin that is poorly soluble in water, supplying a water-soluble polymer solution into first recesses of a first engraved plate, and inserting the puncturing needle parts of the needle-like precursor into the first recesses is described in the following JP2016-106757A. Additionally, a method of manufacturing a percutaneous medicine administration system by filling a mold provided with a plurality of recesses with a solid medicine and combining the solid medicine with a base material is described in JP2015-116335A.

SUMMARY OF THE INVENTION

In the method of manufacturing a needle-like body described in the above JP2016-106757A, the needle parts are formed of the resin that is poorly soluble in water, and the needle-like precursor is formed of the water-soluble resin. Thus, it is difficult to bond the resin, that is poorly soluble in water, and the water-soluble resin together. Additionally, in JP2015-116335A, the molded medicine consisting of the solid medicine and the base material are bonded together with an adhesive. Therefore, firm bonding strength is not obtained.

Additionally, in a case where the percutaneous absorption sheets having a medicine are manufactured as the needle-like array sheets, it is necessary to perform this manufacture in a sterile state using a facility, such as a sterile room, because these sheets are medical products. Since it is necessary to perform drying at a temperature such that the medicine is not decomposed, the drying cannot be dried at high temperature, and substantial time is required for the drying. Moreover, since it is necessary to make a facility, such as a sterile room, wide, in order to enhance productivity in a case where the drying takes time, there is a problem in that facility costs become high.

The invention has been made in view of such circumstances, and an object thereof is to provide a method of manufacturing a needle-like array sheet that has high productivity and is capable of being manufactured at low cost, in a needle-like array sheet of a two-layer configuration in which a desired material is concentrated on a distal end of a needle-like array.

In order to achieve the above object, a method of manufacturing a needle-like array sheet related to the invention is a method of manufacturing a needle-like array sheet comprising a first liquid supply step of supplying a first needle-like array-forming solution consisting of an aqueous solution on a first mold having a first recess with a shape corresponding to a needle-like array; a first liquid drying step of interrupting drying of the first needle-like array-forming solution in a wet state and forming a needle-like distal end part; a second liquid supply step of supplying a second needle-like array-forming solution consisting of an aqueous solution on a second mold having a second recess corresponding to a shape from which a portion of the shape corresponding to the needle-like array is removed; a sheet part molding product forming step of peeling a sheet part molding product from the second mold after the second needle-like array-forming solution is dried and solidified and the sheet part molding product having a protrusion corresponding to the second recess is formed; an insertion step of inserting the protrusion of the sheet part molding product into the first recess of the first mold after the first drying step; an entire drying step of drying and solidifying the needle-like distal end part and the sheet part molding product after the insertion step, bonding the needle-like distal end part and the protrusion of the sheet part molding product together, and forming a needle-like array sheet having the needle-like array; and a peeling step of peeling the needle-like array sheet from the first mold.

According to the method of manufacturing a needle-like array sheet of the invention, the needle-like array sheet is manufactured by forming the sheet part molding product having the protrusion using the second mold, and bonding the needle-like distal end part formed within the first recesses of the first mold, and the protrusion of the sheet part molding product. Hence, since the formation of the sheet part molding product using the second needle-like array-forming solution can be performed in a step different from the step of manufacturing the needle-like array sheet using the first mold, the drying time of the second needle-like array-forming solution can be shortened. Additionally, since the sheet part molding product can be dried only with the second needle-like array-forming solution and can be dried separately from the first needle-like array-forming solution including other components, such as a medicine, it is possible to perform the drying at high temperature regardless of decomposition of the medicine or the like, and the drying time can be shortened.

Moreover, since the first needle-like array-forming solution and the second needle-like array-forming solution consist of the aqueous solutions, and are formed using a water-soluble material, the drying of the needle-like distal end part is interrupted in a wet state, and the needle-like distal end part and the protrusion of the sheet part molding product are bonded together in the entire drying step, the bonding can be firmly performed.

In one aspect of the method of manufacturing a needle-like array sheet related to the invention, it is preferable that the second recess of the second mold has a shape in which a distal end of the first recess of the first mold is filled.

According to this aspect, since a portion formed of the first needle-like array-forming solution can be the distal end part of the first recess, a desired material can be concentrated on the distal end part of the needle-like array sheet manufactured by making the first needle-like array-forming solution contain the desired material.

In one aspect of the method of manufacturing a needle-like array sheet related to the invention, it is preferable that the thickness of the second recess of the second mold is greater than the thickness of the first recess of the first mold.

Since the second needle-like array-forming solution filled into the second recess of the second mold shrinks through the second liquid drying step, the protrusion of the sheet part molding product can be easily inserted into the first recess by making the thickness of the second recess greater than the thickness of the first recess.

In one aspect of the method of manufacturing a needle-like array sheet related to the invention, it is preferable that the first liquid supply step, the first liquid drying step, the insertion step, the entire drying step, and the peeling step are performed under sterile conditions.

According to this aspect, since the above step is performed under sterile conditions, that is, the second liquid supply step and the sheet part molding product forming step may not be performed under sterile conditions, the drying step to be performed under sterile conditions can be shortened. Hence, the costs of a facility brought into a sterile state can be lowered, and the needle-like array sheet can be manufactured without lowering productivity even in a case where the volume of a facility, such as a sterile room, is small.

In one aspect of the method of manufacturing a needle-like array sheet related to the invention, it is preferable that the method further comprises a sterilization step of sterilizing the sheet part molding product after the sheet part molding product forming step.

After the sheet part molding product is formed, the safety of a needle-like array sheet to be manufactured can be ensured even in a case where the second liquid supply step and the sheet part molding product forming step are not performed under sterile conditions by having the sterilization step of sterilizing the sheet part molding product.

In one aspect of the method of manufacturing a needle-like array sheet related to the invention, it is preferable that the second recess of the second mold has a through-hole.

According to this aspect, a second needle-like array-forming solution with high viscosity, that is, high concentration can also be easily supplied onto the second mold by providing the through-hole in the second recess of the second mold and performing the second liquid supply step while performing suctioning from the through-hole. Since the amount of a solvent can be reduced by setting the concentration of the second needle-like array-forming solution to be high, the drying time can be shortened. Additionally, since the drying of the second needle-like array-forming solution can be performed by evaporating the solvent also from the through-hole side, the drying time can be shortened.

According to the method of manufacturing a needle-like array sheet of the invention, by forming the sheet part of the needle-like array sheet to be manufactured and the sheet part molding product that becomes a portion of the needle-like array separately from the distal end part of the needle-like protrusion of the needle-like array, the drying time can be shortened, and the time required for the manufacture of the needle-like array sheet can be shortened. Additionally, productivity can be improved without bringing a facility (sterile room or the like) into a sterile state.

DESCRIPTION OF THE PREFERRED EMBODIMENTS

Hereinafter, a method of manufacturing a needle-like array sheet related to the invention will be described according to the accompanying drawings. In addition, in the present specification, "to" is used in the meaning including numerical values described before and after "to" as lower limits and upper limits.

<Method of Manufacturing Needle-Like Array Sheet>

Figure 1:
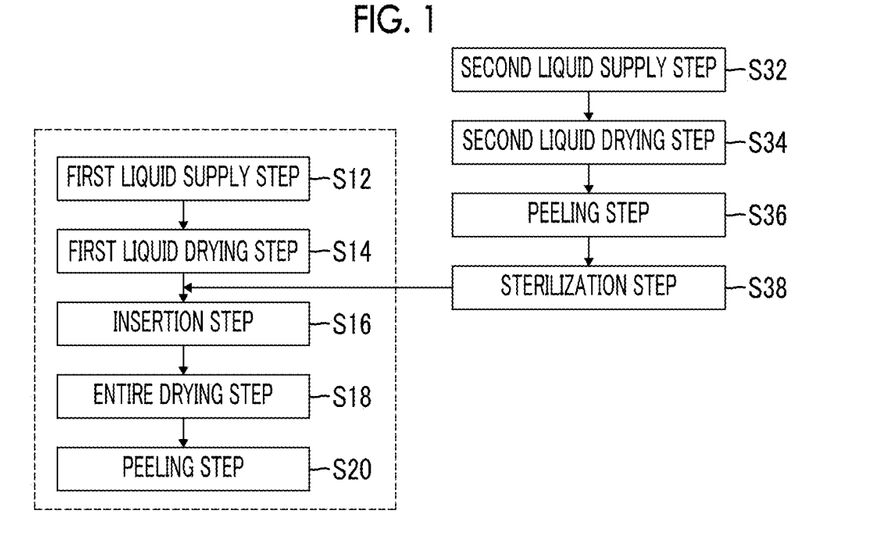
FIG. 1 is a flowchart of a method of manufacturing a needle-like array sheet.

FIG. 1 is a flowchart of the method of manufacturing a needle-like array sheet of the present embodiment. As illustrated in FIG. 1, the method of manufacturing a needle-like array sheet of the present embodiment has a first liquid supply step (Step S12), a first liquid drying step (Step S14), an insertion step (Step S16), an entire drying step (Step S18), and a peeling step (Step S20). Additionally, a sheet part molding product to be inserted into a first mold in the insertion step is formed in another process consisting of a second liquid supply step (Step S32), a second liquid drying step (Step S34), a peeling step (Step S36), and a sterilization step (Step S38). Hereinafter, the respective steps will be described.

[First Liquid Supply Step (Step S12)]

The first liquid supply step is a step of supplying a first needle-like array-forming solution consisting of an aqueous solution on a first engraved plate having a recess of a shape corresponding to the needle-like array to be manufactured. First, a method of manufacturing the first mold will be described with reference to FIGS. 2 to 4.

(Manufacture of First Mold)

Figure 15:
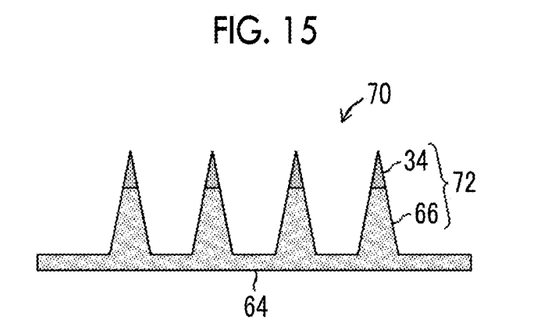
FIG. 15 is a process diagram illustrating the procedure of manufacturing the needle-like array sheet.

A first mold 20 is a mold including first recesses 22, which is a reversal mold of needle-like protrusions 72 of a needle-like array sheet 70 (refer to FIG. 15). The first mold 20 is manufactured using resin from an original plate 10 on which a projection-like pattern 12 is formed.

Figure 2:
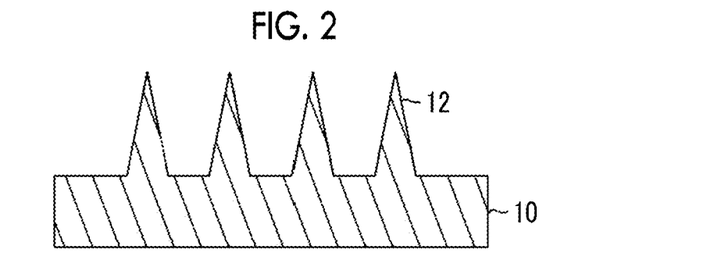
FIG. 2 is a process diagram illustrating a procedure of manufacturing a first mold.

First, as illustrated in FIG. 2, the original plate 10 on which the projection-like pattern 12 is formed is prepared. Although a method of making the original plate 10 on which the projection-like pattern 12 is formed is not particularly limited, for example, the projection-like pattern can be made as follows. A plurality of the projection-like patterns 12 can be made on the surface of the original plate 10 by machining a metal substrate, such as Ni, through machine cutting using a cutting tool, such as a diamond bit.

As another method, exposure and development are performed after a photoresist is coated on a Si substrate. Then, the projection-like pattern 12 is made on the surface of the original plate 10 by performing etching through reactive ion etching (RIE). In addition, in a case where etching, such as the RIE, is performed in order to form the projection-like pattern 12 on the surface of the original plate 10, it is possible to form a projection-like pattern by performing the etching from an oblique direction while rotating the Si substrate.

Figure 3:
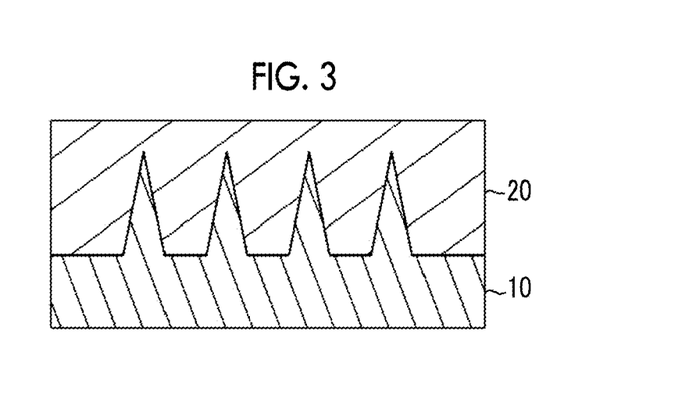
FIG. 3 is a process diagram illustrating the procedure of manufacturing the first mold.
Figure 4:
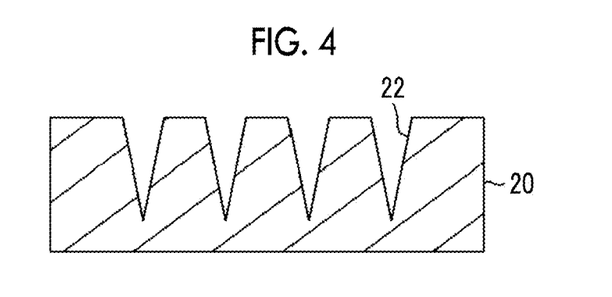
FIG. 4 is a process diagram illustrating the procedure of manufacturing the first mold.

Next, as illustrated in FIGS. 3 and 4, the first mold 20 having the first recesses 22 is manufactured using the original plate 10. As methods of manufacturing the first mold 20, the following methods can be performed using resin. In a first method, the first mold 20 having the first recesses 22, which is a reversal mold of the projection-like pattern 12, is made from the original plate 10 after polydimethylsiloxane (PDMS; for example, silicone resin in which a curing agent is poured into SYLGARD 184 manufactured by Dow Corning Toray Co, Ltd.) is poured into the original plate 10 and is heat-treated and cured at 100° C.

A second method is a method of peeling the first mold 20 from the original plate 10 after ultraviolet curing resin cured by radiating ultraviolet rays is poured into the original plate 10 and is irradiated with ultraviolet rays in a nitrogen atmosphere. A third method is a method of peeling the first mold 20 from the original plate 10 after plastic resin, such as polystyrene or polymethyl methacrylate (PMMA) obtained by dissolving, in an organic solvent, is poured into the original plate 10 on which a release agent is coated, is dried to volatilize the organic solvent, and is cured.

A material for forming the first mold 20 is resin, and it is preferable to use ultraviolet curing resin or thermoplastic resin. By using the ultraviolet curing resin or the thermoplastic resin, the first mold 20 can be easily made, and the projection-like pattern 12 of the original plate 10 can be stably formed.

(First Liquid Supply Step)

Figure 5:
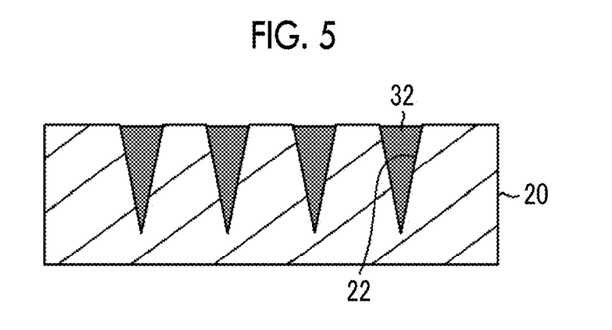
FIG. 5 is a process diagram illustrating a procedure of manufacturing the needle-like array sheet.

Next, the first recesses 22 of the first mold 20 are filled with a first needle-like array-forming solution 32 consisting of an aqueous solution. As a filling method, only the first recesses 22 may be filled with the solution by bringing distal end parts of slit nozzles into contact with the first mold 20. Additionally, the first needle-like array-forming solution 32 may be coated on the first mold 20, and the first recesses 22 may be filled with the first needle-like array-forming solution 32 by bringing a blade into contact with the first mold 20.

A water-soluble material is used as a material of the first needle-like array-forming solution, and is supplied to the first mold 20 as an aqueous solution. It is preferable to use resin with biocompatibility as a material of a resin polymer contained in the first needle-like array-forming solution. As such resin, it is preferable to use saccharides, such as glucose, maltose, pullulan, sodium chondroitin sulfate, sodium hyaluronate, and hydroxyethyl starch, protein, such as gelatin, and biodegradable polymers, such as polylactic acid and a lactic acid-glycolic acid copolymer.

In a case where the needle-like array sheet is used as a percutaneous absorption sheet, a medicine is made to be contained in the first needle-like array-forming solution 32. The medicine is not particularly limited in a case where a function as a medicine is provided, and may include, for example, peptide, protein, nucleic acid, polysaccharide, vaccine, a medicine compound belonging to water-soluble low molecular compound, or a cosmetic component.

Although concentration varies also depending on materials, it is preferable to make the concentration (the concentration of a polymer except for a medicine in a case where the medicine itself is a polymer) of the resin polymer in the first needle-like array-forming solution 32 be 0 to 30 mass %. Additionally, a solvent may be other than water or may contain volatile substances, or in order to shorten drying time, alcohol, such as ethanol, may be contained in the aqueous solution.

As a method of adjusting the first needle-like array-forming solution 32, a resin polymer may be dissolved in water and a medicine may be added after the dissolution, or a resin polymer may be put in and melted in a liquid in which a medicine is dissolved. In a case where it is difficult to dissolve the resin polymer in water, the resin polymer may be heated and dissolved. Although temperature can be appropriately selected depending on the type of resin polymer, it is preferable to heat the resin polymer at a temperature of about 20° C. to 40° C. if necessary. It is preferable that the viscosity of the first needle-like array-forming solution is 200 mPa·s or less with a solution containing a medicine, and it is more preferable that the viscosity is 50 mPa·s or less. By appropriately adjusting the viscosity of the first needle-like array-forming solution, it becomes easy to inject a solution into the first recesses 22 of the first mold 20. For example, the viscosity of the first needle-like array-forming solution can be measured by a capillary viscometer, a falling-ball-type viscometer, a rotational viscometer, or a vibrational viscometer.

[First Liquid Drying Step (Step S14)]

Figure 6:
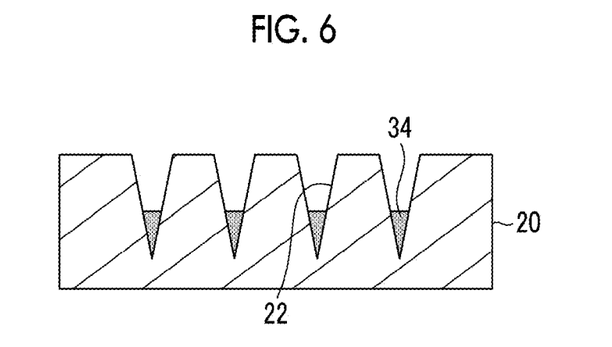
FIG. 6 is a process diagram illustrating the procedure of manufacturing the needle-like array sheet.

Next, as illustrated in FIG. 6, needle-like distal end parts 34 are formed within the first recesses 22 of the first mold 20 by drying the first needle-like array-forming solution 32. The drying can be performed by blowing wind against the first needle-like array-forming solution 32 supplied to the first mold 20.

As will be described below, in the present embodiment, the sheet part molding product is formed in another step, and is inserted into the first recesses 22 of the first mold 20 after a first drying step. In the first liquid drying step, the drying is interrupted in a wet state without completely drying the first needle-like array-forming solution. By interrupting the drying in the wet state and forming the needle-like distal end parts 34, the needle-like distal end parts 34 can be bonded to the sheet part molding product without using an adhesive in a case where being subsequently dried and solidified. In the present embodiment, the "wet state" means that the first needle-like array-forming solution has flowability, and is in a state where this solution can be dried and solidified and thus bonded to protrusions of the sheet part molding product.

<<Formation of Sheet Part Molding Product>>

In the present embodiment, the sheet part molding product is formed using a second mold 50, and the formed sheet part molding product is inserted into the first mold 20 after the first drying step. A method of forming the sheet part molding product will be described below.

[Second Liquid Supply Step (Step S32)]

A second liquid supply step is a step of supplying a second needle-like array-forming solution consisting of an aqueous solution on the second mold having second recesses corresponding to a shape from which a portion of a shape corresponding to a needle-like array of the manufactured needle-like array sheet is removed. First, a method of manufacturing the second mold will be described with reference to FIGS. 7 to 9.

(Manufacture of Second Mold)

Figure 12:
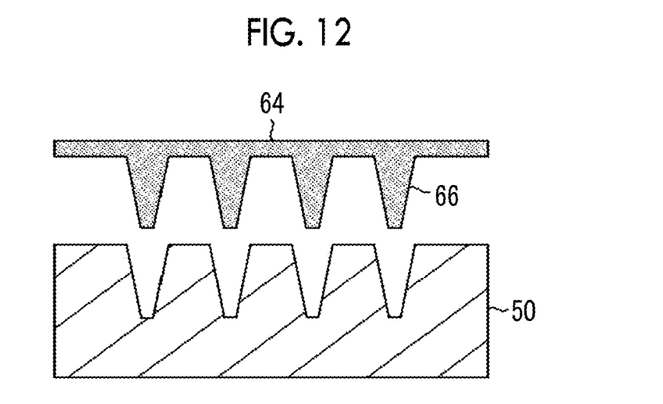
FIG. 12 is a process diagram illustrating the procedure of forming the sheet part molding product.

The second mold 50 is a mold including second recesses 52, which is a reversal mold of protrusions 66 of a sheet part molding product 64 (refer to FIG. 12). The second mold 50 is manufactured using resin from an original plate 40 on which a projection-like pattern 42 is formed.

Figure 7:
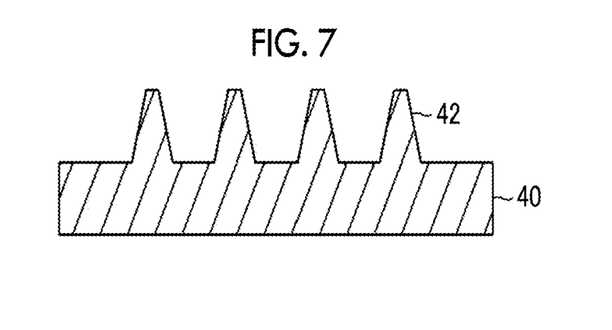
FIG. 7 is a process diagram illustrating a procedure of manufacturing a second mold.

First, as illustrated in FIG. 7, the original plate 40 on which the projection-like pattern 42 is formed is prepared. As a method of making the original plate 40 on which the projection-like pattern 42 is formed, the original place can be made by the same method as the original plate 10 described above. Additionally, the projection-like pattern 42 formed on the original plate 40 is a reversal mold of the second recesses 52 of the second mold 50, and the second recesses 52 correspond to a shape from which a portion of the shape corresponding to the needle-like array is removed. That is, the projection-like pattern 42 formed on the original plate 40 is a shape from which a portion of the projection-like pattern 12 formed on the original plate 10 is removed. Hence, an original plate from which a portion of the projection-like pattern 12 of the original plate 10 on which the projection-like pattern 12 illustrated in FIG. 1 is formed is removed can also be used as the original plate 40 on which the projection-like pattern 42 is formed.

Additionally, it is preferable that the shape of the second recesses 52 of the second mold 50 is a shape in which distal ends of the first recesses 22 of the first mold 20 are filled. By using such a shape as the shape of the second recesses 52, the shape of the protrusions 66 of the sheet part molding product 64 formed using the second mold 50 can be a shape in which distal ends are removed from the shape of the needle-like protrusions of the needle-like array sheet to be manufactured. Then, portions of the removed distal ends can be used as the needle-like distal end parts 34 formed using the first mold 20. Hence, a material contained in the first needle-like array-forming solution can be concentrated on the distal ends of the needle-like protrusions of the needle-like array sheet.

Additionally, it is preferable that the thickness of the second recesses 52 of the second mold 50 is greater than the thickness of the first recesses 22 of the first mold 20. In the second liquid drying step, the second needle-like array-forming solution within the second recesses 52 shrinks and the protrusions 66 of the sheet part molding product 64 to be formed become thin. Therefore, by making the second recesses 52 thick, it is possible to obtain an optimal thickness in a case where the protrusions 66 are inserted into the first recesses 22 in the insertion step.

It is preferable that the size of the first recesses 22 of the first mold 20 and the size of the second recesses 52 of the second mold 50 can be appropriately an optimal dimension according to the concentration of solid component, the drying conditions, or the like of the solution. The size of the first recesses 22 and the size of the second recesses 52 can be, for example, the following sizes. In a case where the shape of needle-like protrusions of the needle-like array sheet to be manufactured is a conical shape, the first recesses 22 can be made to have a shape in which the diameter of openings is 0.4 mm and the height is 0.8 mm. Additionally, the second recesses 52 can be truncated cones with a bottom surface diameter of 0.16 mm, an opening diameter of 0.48 mm, and a height of 0.64 mm.

Figure 8:
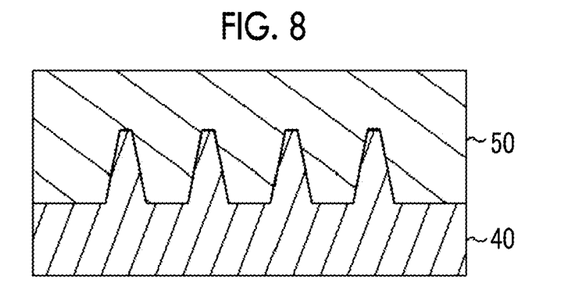
FIG. 8 is a process diagram illustrating the procedure of manufacturing the second mold.
Figure 9:
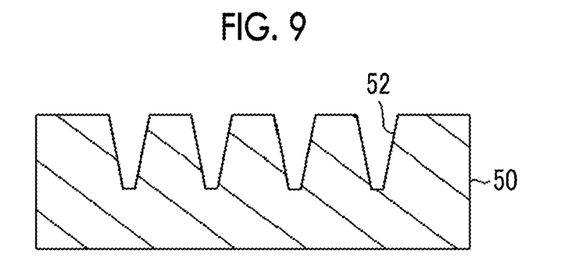
FIG. 9 is a process diagram illustrating the procedure of manufacturing the second mold.

Next, as illustrated in FIGS. 8 and 9, the second mold 50 having the second recesses 52 is made using the original plate 40. As a method of manufacturing the second mold 50, the second mold can manufacture by the same method as the method of manufacturing the first mold 20. Additionally, the same material as the material for forming the first mold 20 can also be used as a material for forming the second mold 50.

(Second Liquid Supply Step)

Figure 10:
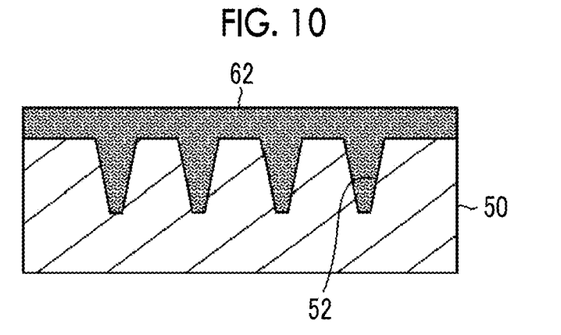
FIG. 10 is a process diagram illustrating a procedure of forming a sheet part molding product.

Next, as illustrated in FIG. 10, a second needle-like array-forming solution 62 consisting of an aqueous solution is coated on the insides and the surfaces of the second recesses 52 of the second mold 50. As a coating method, similar to the first liquid supply step, the second needle-like array-forming solution can be supplied using the slit nozzles. Additionally, another method can be performed by a dispenser. Moreover, in addition to the coating performed by the dispenser, coating, such as bar coating, spin coating, or spraying, can be applied.

It is preferable to use the water-soluble material, similar to the first needle-like array-forming solution, as a material of the second needle-like array-forming solution, and to use resin with biocompatibility as the material of the resin polymer. As a specific example of the resin, the material same as the resin used for the first needle-like array-forming solution can be used. Additionally, the adjustment method and the viscosity of the second needle-like array-forming solution can be the same method and viscosity as those of the first needle-like array-forming solution. Additionally, although the concentration varies also depending on materials, it is preferable to set the concentration such that the resin polymer is contained in the solution at 10 to 50 mass %.

[Second Liquid Drying Step (Step S34)]

Figure 11:
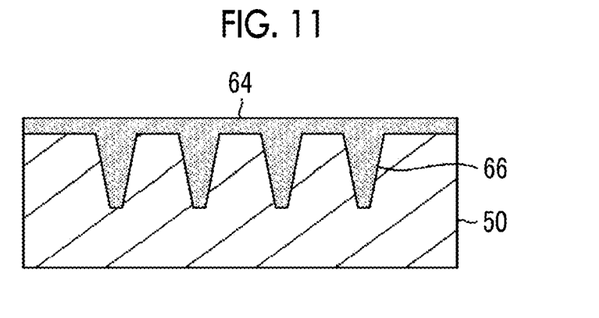
FIG. 11 is a process diagram illustrating the procedure of forming the sheet part molding product.

Next, as illustrated in FIG. 11, the sheet part molding product 64 formed with the protrusions 66, which is a reversal mold of the second recesses 52 of the second mold 50, is formed by drying and solidifying the second needle-like array-forming solution 62. The drying and the solidifying can be performed by blowing wind against the second needle-like array-forming solution 62 coated on the second mold 50. Additionally, in the second liquid drying step, it is possible to achieve rapid drying by performing drying at high temperature (for example, 80° C.). This is because medicine is not contained in the second needle-like array-forming solution, and thus the effect of the medicine is lost even in a case where high-temperature drying is performed.

[Peeling Step (Step S36)]

Next, as illustrated in FIG. 12, the sheet part molding product 64 is peeled from the second mold 50. The second liquid drying step and the peeling step are equivalent to a sheet part molding product forming step. A method of peeling the sheet part molding product 64 from the second mold 50 is not particularly limited. During the peeling, it desired that the protrusions 66 are not bent or broken. For example, after a sheet-like base material in which a sticky adhesion layer is formed on the sheet part molding product 64, a method of installing a suction cup on the base material and pulling up the sheet part molding product vertically while suctioning the sheet part molding part with air can be applied. By vertically pulling up the sheet part molding product, the protrusions 66 can be operated from being bent or broken during peeling. Additionally, the base material can also be peeled so as to be turned over from an end part.

Additionally, in FIGS. 10 to 12, although the method of forming the sheet part molding product for each patch is described, a sheet part molding product can be formed with a large number of patches, for example, the number of 5×5 patches. However, in the insertion step to be described below, it is difficult to accurately insert the sheet part molding product with a large number of patches into in the first mold with a large number of patches, and alignment is also difficult. Therefore, it is preferable to insert the sheet part molding product for each patch or with a size of at most 2×2 patches. By using the sheet part molding product with the above size, the sheet part molding product can be easily inserted into the first mold in the insertion step. In this case, it is preferable to have a cutting step of cutting the sheet part molding product for each patch or with a predetermined patch size to be used in the insertion step after the peeling step.

[Sterilization Step (Step S38)]

Next, sterilization treatment of the sheet part molding product 64 peeled from the second mold 50 is performed. The peeled sheet part molding product 64 is inserted into the first mold 20 in which the needle-like distal end parts 34 dried in a wet state are formed. In a case where the needle-like array sheet is a percutaneous absorption sheet, a medicine is contained in the first needle-like array-forming solution, and the medicine is administered to the body via the skin during use. Therefore, it is preferable that the first liquid supply step and the first liquid drying step are performed under sterile conditions. Hence, it is preferable that the sterilization treatment is also performed on the sheet part molding product 64 after molding. The sterilization treatment can be performed by radiating electron rays or γ rays.

[Insertion Step (Step S16)]

Figure 13:
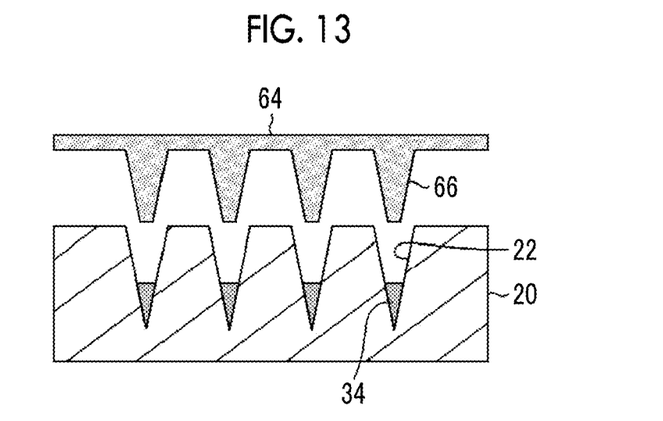
FIG. 13 is a process diagram illustrating the procedure of manufacturing the needle-like array sheet.

Next, as illustrated in FIG. 13, the protrusions 66 of the sheet part molding product 64 are inserted in the first recesses 22 of the first mold 20 in which the needle-like distal end parts 34 are formed by the first liquid drying step (Step S14). In a case where the sheet part molding product 64 is inserted, it is preferable that the sheet part molding product 64 is handled so as not to be broken while holding a sheet surface (a surface opposite to the surface on which the protrusions 66 are formed) of the sheet part molding product 64 with a vacuum chuck or the like. Through the insertion step, the needle-like distal end parts 34 in the wet state and the protrusions 66 of the sheet part molding product 64 can be brought into contact with each other.

[Entire Drying Step (Step S18)]

Figure 14:
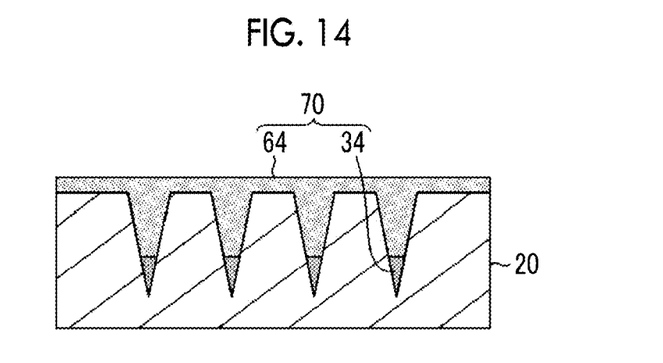
FIG. 14 is a process diagram illustrating the procedure of manufacturing the needle-like array sheet.

Next, as illustrated in FIG. 14, by drying the entirety of the sheet part molding product 64 and the needle-like distal end parts 34 in a state where these are brought into contact with each other, so that the needle-like distal end parts 34 in the wet state are completely dried and solidified. Accordingly, the needle-like distal end parts 34 and the protrusions 66 of the sheet part molding product 64 can be bonded together.

In the present embodiment, the needle-like distal end parts 34 are formed of the first needle-like array-forming solution 32 consisting of an aqueous solution, and the sheet part molding product 64 is formed of the second needle-like array-forming solution 62 consisting of an aqueous solution. Thus, both of these needle-like distal end parts are formed of the water-soluble materials. Hence, the needle-like distal end parts 34 and the protrusions 66 of the sheet part molding product 64 can be firmly bonded together by drying the needle-like distal end parts 34 in the wet state.

[Peeling Step (Step S20)]

In the sheet part molding product 64 in which the needle-like distal end parts 34 are bonded by the entire drying step (Step S18), the needle-like array sheet 70 is manufactured by being peeled from the first mold 20 (FIG. 15). A method of peeling the needle-like array sheet 70 from the first mold 20 is not particularly limited. For example, the above-described sheet part molding product 64 can be performed by the same method as the method of being peeled from the second mold 50. During the peeling, it is desired that the needle-like protrusions 72 consisting of the needle-like distal end parts 34 and the protrusions 66 are not bent or broken.

Figure 16:
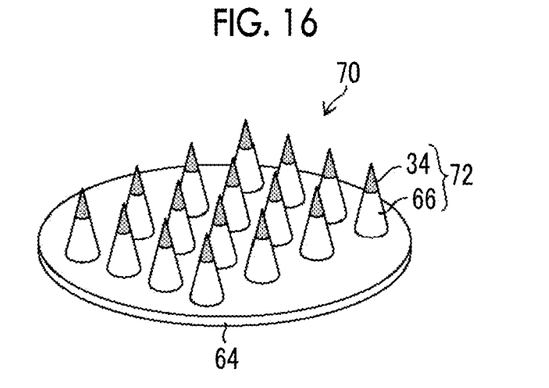
FIG. 16 is a perspective view of the needle-like array sheet.

FIG. 16 is a perspective view of the needle-like array sheet. In the needle-like array sheet of the present embodiment, the needle-like protrusions 72 are disposed in an array and form one patch. In FIG. 16, although the needle-like protrusions 72 are disposed in a 4×4 an array and form one patch, the number of needle-like protrusions 72 is not limited to this.

The shape of the needle-like protrusions 72 of the needle-like array sheet 70 to be manufactured is not particularly limited in a case where the distal ends thereof have a tapered shape. In FIG. 16, although the shape of the needle-like protrusions 72 is a conical shape, a pyramidal shape, such as a triangular pyramid or a pyramid, may be adopted. Additionally, the shape of the needle-like protrusions 72 can be formed by a tapered needle part and a frustum part connected to the needle part.

The height of the needle-like protrusions 72 is within a range of 100 μm or more and 2000 μm or less, and preferably, 200 μm or more and 1500 μm or less.

In the needle-like protrusions 72 of the needle-like array sheet 70 to be manufactured, the needle-like distal end parts 34 are a duplicate of the projection-like pattern 12 of the original plate 10 and the protrusions 66 is a duplicate of the projection-like pattern 42 of the original plate 40. Therefore, the needle-like protrusions 72 of the needle-like array sheet 70 to be manufactured can be formed in a desired shape by forming the shape of the projection-like pattern 12 of the original plate 10 and the projection-like pattern 42 of the original plate 40 in a desired shape.

In the related-art method of manufacturing a needle-like array sheet, after the first needle-like array-forming solution is coated on the same mold and is dried if necessary, the second needle-like array-forming solution is coated and dried. In order not to mix the first needle-like array-forming solution and the second needle-like array-forming solution together, it is necessary to perform drying after the respective solutions are applied. Additionally, since a medicine is decomposed in a case where there is the medicine in the first needle-like array-forming solution, the second needle-like array-forming solution cannot be dried at high temperature, and substantially times is taken for the drying. Moreover, in a case where the needle-like array sheet is a medical product, such as a percutaneous absorption sheet, it is necessary to perform a manufacturing step under sterile conditions, for example, it is necessary to perform all steps within an isolator. In order to improve productivity, a large isolator facility is required, which is an expensive facility. As the drying time, 40 to 80 minutes are required for the drying of the first needle-like array-forming solution, and 200 to 600 minutes are required for the drying of the second needle-like array-forming solution.

According to the method of manufacturing a needle-like array sheet of the present embodiment, the needle-like array sheet 70 is manufactured by forming the sheet part molding product 64 using the second mold 50, and bonding the needle-like distal end parts 34 in the wet state formed within the first recesses 22 of the first mold 20, and the sheet part molding product 64 together.

First, in the drying (first liquid drying step) of the first needle-like array-forming solution, it is necessary to interrupt the drying in the wet state. Therefore, the drying can be finished in a time shorter than the related-art drying time. For example, the first liquid drying step can be performed in 10 to 20 minutes. Also, since medicine is not provided in the drying (second liquid drying step) of the second needle-like array-forming solution, the drying can be performed out of the isolator, the drying can be performed at high temperature, and the drying time can be omitted. Also, in the entire drying step in which the needle-like distal end parts 34 and the sheet part molding product 64 are bonded together, the needle-like distal end parts 34 which have been somewhat dried in the first liquid drying step, are dried and solidified. Therefore, the drying can be performed in a short time. The time for the entire drying step can be, for example, 20 to 40 minutes.

Hence, in the present embodiment, it is preferable to perform Step S12 to Step S20 within the isolator (under sterile conditions). Therefore, the drying time of a step performed within the isolator can be shortened, the manufacturing time of the needle-like array sheet can be shortened. Additionally, by shortening the time for the step performed within the isolator, a wide facility becomes unnecessary and facility costs can be lowered.

Moreover, since the sheet part molding product formed of the second needle-like array-forming solution comes in contact in a solidified state, diffusion of the first needle-like array-forming solution into the second needle-like array-forming solution can be suppressed, and components contained in the first needle-like array-forming solutions can be concentrated at the distal ends of the needle-like protrusions 72.

<<Other Methods of Forming Sheet Part Molding Product>>

FIGS. 17 to 20 are process diagrams illustrating other methods of forming sheet part molding products. The methods of forming the sheet part molding products illustrated in FIGS. 17 to 20 are different from the above forming method in that the shapes of the second mold 150 used for the formation of the sheet part molding products are different from each other.

Figure 17:
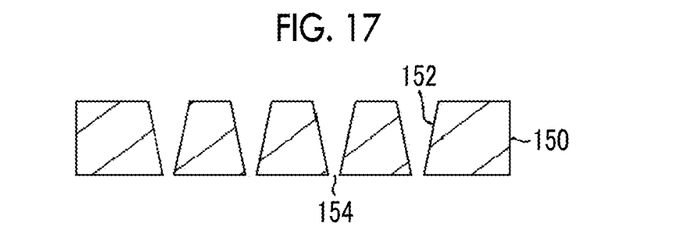
FIG. 17 is a process diagram illustrating another procedure of forming a sheet part molding product.
Figure 18:
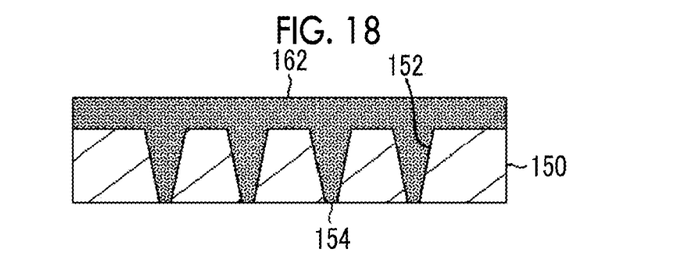
FIG. 18 is a process diagram illustrating still another procedure of forming a sheet part molding product.

As illustrated in FIG. 17, the second mold 150 used in the present embodiment is a mold having through-holes 154 in which the second recesses 152 pass through the second mold 150. By using the through-hole mold as the second mold 150 and performing suction from the through-holes 154 in the second liquid supply step (FIG. 17), the second needle-like array-forming solution 162 can be filled into the second recess 152 even in a case where the viscosity thereof is high. Hence, since the second needle-like array-forming solution 162 can be a solution containing a resin polymer in high concentration, and the amount of the solvent can be reduced, the drying time can be shortened.

Additionally, also in the second liquid drying step (FIG. 18), the solvent can be dried from the through-holes 154 side of the second mold 150. Thus, the drying time can be shortened.

Figure 19:
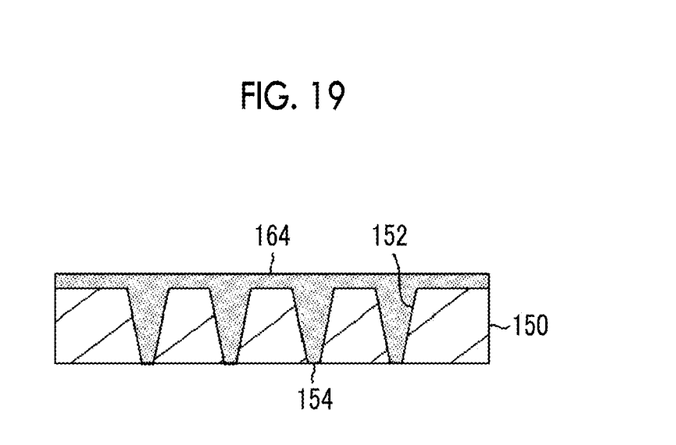
FIG. 19 is a process diagram illustrating a still further procedure of forming a sheet part molding product.
Figure 20:
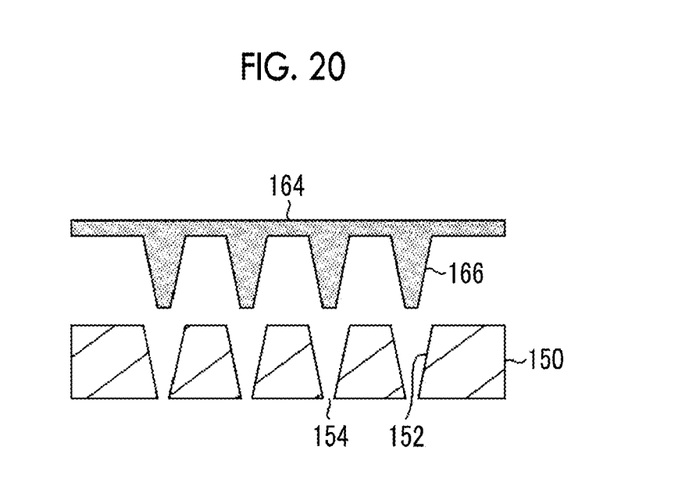
FIG. 20 is a process diagram illustrating a still further procedure of forming a sheet part molding product.

By peeling the sheet part molding product 164 from the second mold 150 after the second liquid drying step, the sheet part molding product 164 having protrusions 166, which is a reversal mold of the second recesses 152, can be formed (FIG. 19). Also regarding the sheet part molding product 164 in this way, the sterilization step is performed if necessary and is used for the manufacture of the needle-like array sheet.

EXPLANATION OF REFERENCES

10, 40: original plate
12, 42: projection-like pattern
20: first mold
22: first recess
32: first needle-like array-forming solution
34: needle-like distal end part
50, 150: second mold
52, 152: second recess
62, 162: second needle-like array-forming solution
64, 164: sheet part molding product
66, 166: protrusion
70: needle-like array sheet
72: needle-like protrusion
154: through-hole

What is claimed is:

1. A method of manufacturing a needle-like array sheet, comprising:
   a first liquid supply step of supplying a first needle-like array-forming solution consisting of an aqueous solution on a first mold having a first recess with a shape corresponding to a needle-like array;
   a first liquid drying step of partially drying the first needle-like array-forming solution and forming a needle-like distal end part;
   a second liquid supply step of supplying a second needle-like array-forming solution consisting of an aqueous solution of a water-soluble material on a second mold having a second recess corresponding to a shape from which a portion of the shape corresponding to the needle-like array is removed;
   a sheet part molding product forming step of peeling a sheet part molding product from the second mold after the second needle-like array-forming solution is dried and solidified and the sheet part molding product having a protrusion corresponding to the second recess is formed;

an insertion step of inserting the protrusion of the sheet part molding product into the first recess of the first mold after the first liquid drying step, wherein the needle-like distal end part is in a wet state and in contact with the protrusion of the sheet part molding product;

an entire drying step of drying and solidifying the needle-like distal end part and the sheet part molding product after the insertion step, bonding the needle-like distal end part and the protrusion of the sheet part molding product together, and forming a needle-like array sheet having the needle-like array; and a peeling step of peeling the needle-like array sheet from the first mold.

2. The method of manufacturing a needle-like array sheet according to claim 1,
wherein the second recess of the second mold has a shape in which a distal end of the first recess of the first mold is filled.

3. The method of manufacturing a needle-like array sheet according to claim 1,
wherein a thickness of the second recess of the second mold is greater than a thickness of the first recess of the first mold.

4. The method of manufacturing a needle-like array sheet according to claim 1,
wherein the first liquid supply step, the first liquid drying step, the insertion step, the entire drying step, and the peeling step are performed under sterile conditions.

5. The method of manufacturing a needle-like array sheet according to claim 1, further comprising
a sterilization step of sterilizing the sheet part molding product after the sheet part molding product forming step.

6. The method of manufacturing a needle-like array sheet according to claim 1,
wherein the second recess of the second mold has a through-hole.

7. The method of manufacturing a needle-like array sheet according to claim 1,
wherein the sheet part molding product comprises saccharides or proteins.

* * * * *